ly of Germany

United States Patent [19]
Ehrhardt et al.

[11] Patent Number: 5,877,144
[45] Date of Patent: Mar. 2, 1999

[54] ALIPHATIC CARBOXYLATE ESTERS OF INULIN

[75] Inventors: Sonja Ehrhardt, Grob-Gerau; Alireza Haji Begli, Ramsen; Markwart Kunz, Worms; Linda Scheiwe, Braunschweig, all of Germany

[73] Assignee: Sudzucker Aktiengesellschaft Mannheim/Ochsenfurt, Mannheim, Germany

[21] Appl. No.: 807,337

[22] Filed: Feb. 28, 1997

[30] Foreign Application Priority Data

Mar. 1, 1996 [DE] Germany .................. 196 07 847.4

[51] Int. Cl.[6] ...................................................... C11D 3/22
[52] U.S. Cl. ................... 510/470; 510/130; 510/220; 510/235; 510/474; 510/505; 510/514; 536/119; 536/124; 536/115
[58] Field of Search ............... 210/198.2, 502.1, 210/635, 656; 536/119, 48, 115; 510/130, 220, 235, 470, 474, 505, 514

[56] References Cited

U.S. PATENT DOCUMENTS

| | | | |
|---|---|---|---|
| 3,059,011 | 10/1962 | Baur ......................................... | 260/428 |
| 3,697,644 | 10/1972 | Laiderman ................................ | 424/70 |
| 4,226,981 | 10/1980 | Onda et al. ............................... | 536/66 |
| 5,447,643 | 9/1995 | Kelkenberg et al. ..................... | 252/8.6 |
| 5,602,265 | 2/1997 | van den Kommer et al. ........... | 554/211 |

FOREIGN PATENT DOCUMENTS

| | | |
|---|---|---|
| 388 572 A 1 | 9/1990 | European Pat. Off. . |
| 470 870 A 1 | 2/1992 | European Pat. Off. . |
| 03-197409 | 8/1991 | Japan . |
| WO 95/04122 | 2/1995 | WIPO . |
| WO 96/20266 | 7/1996 | WIPO . |

*Primary Examiner*—Paul Lieberman
*Assistant Examiner*—Gregory E. Webb
*Attorney, Agent, or Firm*—Darby & Darby

[57] ABSTRACT

The invention relates to aliphatic carboxylate esters of long-chain inulin, to methods for synthesizing them and to their use as surface-active substances.

22 Claims, No Drawings

ALIPHATIC CARBOXYLATE ESTERS OF INULIN

FIELD OF THE INVENTION

The invention relates to aliphatic carboxylate esters of longer-chain inulin, to methods of synthesizing them, and to their use.

BACKGROUND OF THE INVENTION

Carbohydrates and their compounds have long been used in different areas. However, there continues to be a need to develop new carbohydrate-based compounds, which are distinguished by improved properties such as an increased surface activity.

The linear polydisperse carbohydrate, inulin, consists of a chain of β-2-1-linked furanoid fructose units, which is terminated at the reducing end by an α-D glucose molecule. It occurs in composites, such as chicories, Jerusalem artichoke, dahlias and artichokes as well as in other types of plants, in which it serves as a storage material. It is isolated in economically significant amounts from chicories and Jerusalem artichokes. Depending on the type of plant and on the harvesting time, inulin has different molecular weight distributions and different average chain lengths between 8 and 25. The size of individual molecules ranges, in general, from 5 to 50 monosaccharide units per chain. There are, however, native inulins having an average chain length greater than 25 and correspondingly longer individual chains. Industrially, inulin is used primarily in the food sector for such purposes as the production of diabetic bread and fructose syrup.

Of the known carbohydrate esters based on polysaccharides, only starch and cellulose esters are used industrially. Starch esters, particularly the acetates, are used as sizing agents in the textile area, as surface glue in the paper industry, as thickeners in the film and fiber industry as well as in the food area and for molding. Of the cellulose esters, the synthesis of which is very costly because of the difficulty of dissolving the starting material, the acetates and their mixed esters with propionate and butyrate are of industrial interest. Of the low molecular weight carbohydrate esters, sucrose esters are particularly used, especially the acetates and the mono-fatty acid and di-fatty acid esters. Sucrose acetates and mixed esters with a high degree of substitution are used as bleaching agent activators and as plasticizers or softeners. Monoesters of sucrose and fatty acids are used as surfactants in detergents and as emulsifiers.

Carbohydrate esters can be synthesized in various ways. In solvent methods, the carbohydrate, in the presence of a basic catalyst in a solvent such as dimethylformamide or dimethyl sulfoxide, is reacted with methyl esters of fatty acids. In microemulsion methods, the fatty acid ester is dispersed in a solution of the carbohydrate by means of an emulsifier, for example, using the corresponding alkali salt of the fatty acid. The solvent is removed before the actual reaction. Finally, transesterification can take place directly in the melt of the carbohydrate and the fatty acid ester employing basic catalysis. Conducting the reaction of these known methods and working up the compounds is expensive. The reaction parameters of pressure and temperature must frequently be varied. In order to isolate the product, several extraction and distillation steps are required. Furthermore, in view of the high thermal stress on the products, there is danger of discoloration.

Little is known about the synthesis and use of inulin esters. Japanese patent No. 63,287,710 describes the peracetylation of the inulin chain in dimethylformamide/pyridine. Pringsheim et al., *Chem. Ber.* (1921), 54, 1281, describe the peracetylation of the inulin chain in pyridine. The peracetate shows adhesive properties, is water resistant and is therefore proposed for use in the cosmetics area. Schacht et al., *Journal of Controlled Release*, (1985), 2, 245, describe the use of succinoylated inulin as a carrier material for pharmaceutical products.

The compounds described are distinguished in that they possess only a slight surface activity or are difficult to synthesize. Surfactants, synthesized from petrochemicals, have the disadvantage of limited availability, and their synthesis, moreover, is environmentally compatible only to a limited extent.

The technical problem for which the present invention provides a solution is to make available surface active carbohydrate compounds which overcome the aforementioned disadvantages and, in particular, are easily synthesized and environmentally compatible and, furthermore, because of their surface active properties, are suitable for a plurality of uses.

SUMMARY OF THE INVENTION

The present invention provides inulin esters having particularly advantageous physical properties, including solubility and surface activity, that make them suitable for use in a wide variety of industrial and pharmaceutical applications.

According to the invention, inulin esters are synthesized having an average chain length of at least 6, and preferably 6 to 50, monosaccharide units linked together, though molecules having greater than 50 units are also possible. The inulin esters according to the invention are esterified via at least one of their hydroxyl groups with a saturated carboxylic acid having 2 to 22 carbon atoms, preferably 2 to 7 carbon atoms. Suitable carboxylic acids encompass branched and unbranched carboxylic acids, including without limitation, acetic acid, propionic acid, butyric acid, isobutyric acid, valeric acid, caproic acid, heptanoic acid, caprylic acid, capric acid, lauric acid, myristic acid, palmitic acid, stearic acid, arachidic acid and behenic acid. The degree of substitution (defined as the molar ratio of monosaccharide units to alkyl substituents) ranges between 0.3 and 3, and is preferably less than 1 and most preferably less than or equal to 0.5. In a given preparation, the inulin may be esterified at at least two hydroxyl groups with different or identical carboxylic acids.

The invention also provides methods for synthesizing the above-described inulin esters. According to the invention, chlorides or anhydrides of suitable carboxylic acids are reacted with inulin in the presence or absence of solvents and/or catalysts. In a preferred embodiment, methyl or ethyl esters of carboxylic acids having 2 to 22 carbon atoms are reacted with inulin having an average chain length of at least 6, and preferably 6 to 50, in the absence of solvents, using a kneader and preferably an extruder to reduce the thermal burden.

The invention also provides aqueous solutions and powders comprising the inulin esters described above. Also encompassed by the invention are cosmetic products, including without limitation cleansing creams, hair rinses, and body lotions; and rinsing agents such as, for example, dishwashing detergent.

DETAILED DESCRIPTION OF THE INVENTION

All patent applications, patents, and literature references cited in this specification are hereby incorporated by reference in their entirety. In the case of inconsistencies, the present description, including definitions, will control.

The present invention provides inulin esters whose surface activity and other physical properties can be predictively manipulated to produce compounds useful for a variety of different applications. The invention also encompasses methods for the synthesis of these inulin esters; compositions and products that comprise these inulin esters as surface active substances; and methods for their use.

In particular, the invention relates to inulin esters, comprising at least 6 and preferably 6 to 50, but also more than 50 mutually linked monosaccharide units (fructose units and terminal glucose), at least one of the hydroxyl groups of the inulin being esterified with a saturated carboxylic acid having 2 to 22 carbon atoms. As used herein, "inulin having 6 to 50 mutually linked fructose units" is understood to be an inulin preparation having an average chain length of 6 to 50 units, but which can also have a chain length of more than 50 units, even more than 200 monosaccharide units. It will be understood that the actual average chain length of a given preparation may deviate slightly from the range given; these variations are well known to those skilled in the art.

The carboxylic acid which is esterified to the inulin esters of the invention comprises 2 to 22 carbon atoms and includes branched and unbranched carboxylic acids, including without limitation, acetic acid, propionic acid, butyric acid, isobutyric acid, valeric acid, caproic acid, heptanoic acid, caprylic acid, capric acid, lauric acid, myristic acid, palmitic acid, stearic acid, arachidic acid or behenic acid.

The inulin esters of the present invention are advantageous particularly because their possible applications can be controlled selectively to a large extent by the degree of substitution (DS) and by the nature of the substituents. A low degree of substitution brings about a high surface activity. Moreover, the inulin compounds have an advantage over sucrose esters in that a larger number of hydroxyl functions is available for the substitution. By these means, the ratio of hydrophilicity to hydrophobicity can be varied greatly and, with that, the possible applications expanded with hardly any change in solubility. Compared to starch esters, the inulin compounds of the invention are advantageous in that they can be synthesized from a uniform raw material. Moreover, they are more soluble than cellulose esters and, therefore, can be processed more easily. Finally, the inulin esters of the invention, in contrast to known surfactants from petrochemicals, are composed only of raw materials that can be regenerated and therefore are biologically compatible. Because of their high surface activity, they can be used, for example, either alone or as mixtures, as surfactants in the laundry detergents, dishwashing detergents and in other detergent areas, as well as in cosmetics, as emulsifiers in the food and pharmaceuticals area and as additives in the textile, paper and paint areas.

In a particularly preferred embodiment, the invention provides insulin esters having a degree of substitution less than 1 and preferably less than or equal to 0.5. In inulin, the degree of substitution (DS), which is to be regarded as an average value, represents the molar ratio of fructose glucose units to alkyl substituents. (This DS cannot be higher than 3, since 3 hydroxyl groups per monosaccharide unit are available for the substitution.) Values smaller than 1 indicate that, on the average, not every fructose or glucose unit has been substituted. Pursuant to the invention, therefore, provisions have been made, in particular, that not only fructose units of the inulin chain, but also (and only) the terminal glucose unit can be substituted. The preferred inulin esters of the invention with a low degree of substitution are distinguished in an advantageous manner by their water solubility, as a result of which their synthesis and use are simplified appreciably and, nevertheless, a high surface activity is achieved. They are therefore particularly suitable as surfactants.

The invention also provides inulin esters that contain, on the average, at least 6, preferably 6 to 50, but also more than 50 fructose monosaccharide units linked together, at least one of the hydroxyl groups of the inulin being esterified with a saturated carboxylic acid having 2 to 7 carbon atoms. In a particularly preferred embodiment, the inulin chain is esterified with short-chain branched and unbranched carboxylic acids. Preferred carboxylic acids include without limitation acetic acid, propionic acid, butyric acid, isobutyric acid, valeric acid, caproic acid or heptanoic acid. The advantages of these inulin esters with short-chain carboxylic acid groups and a low to average DS lie in their high effectiveness in decreasing the surface tension of water. Furthermore, these esters form micelles already at low concentrations, making them particularly suitable as additives in detergents. Furthermore, such inulin esters with a high degree of substitution (DS>1), for example, have a low tendency to migrate in films and sheets and are therefore particularly suitable for use as plasticizers.

The invention also encompasses inulin esters having the characteristics described above in which at least two hydroxyl groups are esterified with identical or different carboxylic acids.

The invention also encompasses aqueous solutions and powders which contain an inulin ester according to the present invention.

In a particularly preferred embodiment, the invention provides rinsing agents, including without limitation detergents for washing dishes by hand; and cosmetic products, including without imitation cleansing creams, hair conditioners, and body lotions, which contain one or more of the above-described inulin esters, such as, for example, inulin laurate (with a DS, for example, of 0.04), inulin palmitate (with a DS, for example of 0.04) and inulin stearate (with a DS, for example, of 0.04).

Synthetic Methods

The present invention encompasses methods for synthesizing the aforementioned inulin esters, in which inulin, having at least 6 and preferably 6 to 50, but also more than 50 fructose units linked together, is reacted with chlorides or anhydrides of carboxylic acids having 2 to 22 and preferably 2 to 7 carbon atoms or with mixtures thereof, pyridine being the only solvent.

The invention also provides a method for synthesizing inulin esters, in which the inulin, having at least 6 and preferably 6 to 50, but also more than 50 fructose units linked together, is reacted with anhydrides of carboxylic acids having 2 to 22 and preferably 2 to 7 carbon atoms or with mixtures thereof, pyridine being the only solvent.

Finally, the invention provides a method for synthesizing inulin esters, in which an inulin, having at least 6 and preferably 6 to 50, but also more than 50 fructose units linked together, is reacted with anhydrides of carboxylic acids having 2 to 22 and preferably 2 to 7 carbon atoms or with mixtures thereof, the reaction being carried out in the absence of a solvent.

The invention also relates to a method for synthesizing inulin esters, in which an inulin, having at least 6 and preferably 6 to 50, but also more than 50 fructose units linked together, is reacted in the absence of a solvent with methyl or ethyl esters of carboxylic acids having 2 to 22 carbon atoms, preferably in kneaders and particularly in extruders. The reaction can be improved particularly through the use of esters of carboxylic acids having 12 to 22 carbon atoms. Due to the kneader or, particularly, due to the extruder, the thermal burden is reduced and the aforementioned difficulties of the melt method are avoided.

The compounds of the invention are thus synthesized by reacting inulin with an average chain length of 6 and preferably between 6 and 50, but also one of more than 50, with chlorides or anhydrides of carboxylic acids having 2 to 22 and preferably 2 to 7 carbon atoms in the presence or absence of a solvent and with or without a catalyst. When methyl esters of $C_2$ to $C_{22}$ and preferably of $C_{12}$ to $C_{22}$ carboxylic acids are used, they are reacted with inulin with an average chain length of 60, preferably of between 6 and 50, but also of more than 50 in the absence of a solvent and in the presence of a catalyst.

Inulin esters synthesized pursuant to the invention are obtained as colorless products, the profile of the properties of which is determined by the nature of the substituents and by the degree of substitution. The degree of substitution can be varied from 0.03 to 3 by the molar ratio of the educts, degrees of substitution of less than 1 and, in particular, of not more than 0.5 being preferred.

The invention furthermore provides that inulin is esterified in pyridine, in water or in the absence of a solvent with (i) carboxylic acid anhydrides in the presence of a catalyst or (ii) with carboxylic acid chlorides in pyridine with or without a catalyst, preferably in a quantitative ratio of inulin to anhydride or of inulin to chloride of 36:1 to 8:1.

Carboxylic acids of which anhydrides or acid chlorides may be used include without limitation acetic acid, propionic acid, isobutyric acid, butyric acid, valeric acid, caproic acid, heptanoic acid, caprylic acid, capric acid, lauric acid, myristic acid, palmitic acid, stearic acid, arachidic acid or behenic acid, or mixtures thereof.

In the kneading or extruding method, inulin is esterified with methyl or ethyl esters of $C_2$ to $C_{22}$ and, preferably $C_{12}$ to $C_{22}$ carboxylic acids, preferably in a quantitative ratio of inulin to ester of 36:1 to 1:8 in the absence of a solvent and the presence of a catalyst.

Carboxylic acids of which esters, particularly methyl or ethyl esters may be used include without limitation lauric, myristic, palmitic, stearic, arachidic or behenic.

Synthesis of the inulin esters can be carried out in the presence of a catalyst. Suitable basic or acidic catalysts include without limitation 4-(dimethylamino)-pyridine, sodium acetate, potassium carbonate, ion exchange resins in the acidic or basic form or pyridine and other basic compounds.

The esterification is carried out in the absence of a solvent at temperatures from 100° to 150° C. and, in the presence of solvents, at temperatures from 20° to 100° C. and preferably from 25° to 60° C.

The products are identified by IR and NMR spectroscopy, the following values being characteristic:

IR Signals: The stretching vibration of the alkyl substituents is at 2940 cm$^{-1}$, the carbonyl stretching of the esters is at 1750 cm$^{-1}$, and the carbon-oxygen stretching vibration lies between 1100 cm$^{-1}$ and 1300 cm$^{-1}$.

$^1$H NMR Signals: The resonance signals of the alkyl substituents are at 2.3 ppm and between 0.8 ppm and 1.6 ppm, while the signals of the inulin chain are between 3.4 ppm and 5.7 ppm.

$^{13}$C NMR Signals: The carbonyl carbon signals lie in the region from 172 to 180 ppm, the signals of the alkyl substituents lie in the region from 15 to 30 ppm, and the signals of the inulin chain lie in the regions from 102 to 105 ppm, 72 to 82 ppm and 60 to 63 ppm.

The degree of substitution is determined from the proton ratio of substituent and inulin, which is obtained by integrating the $^1$H NMR signal.

The following are intended as non-limiting examples of the invention:

EXAMPLE 1

Esterification of Inulin with Acetic Anhydride in Pyridine

In a temperature-controlled reactor with stirrer, 21 g (0.13 moles) of inulin, dissolved in 140 mL of pyridine, are mixed with 1.2 mL (0.013 moles) of acetic anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 85% by weight. The degree of substitution is 0.03 and the surface tension of a 1% by weight solution is 66.43 mN/m.

Inulin acetates with other degrees of substitution can be synthesized similarly by varying the amount of acetic anhydride.

EXAMPLE 2

Esterification of Inulin with Butyric Anhydride in Pyridine

In a temperature-controlled reactor with stirrer, 21 g (0.13 moles) of inulin, dissolved in 140 niL of pyridine, are mixed with 2.1 mL (0.013 moles) of butyric anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 85% by weight. The degree of substitution is 0.06 and the surface tension of a 1% by weight solution is 54.95 mN/m.

EXAMPLE 3

Esterification of Inulin with Caproic Anhydride in Pyridine

In a temperature-controlled reactor with stirrer, 21 g (0.13 moles) of inulin, dissolved in 140 mL of pyridine, are mixed with 2.6 mL (0.013 moles) of caproic anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 75% by weight. The degree of substitution is 0.04 and the surface tension of a 1% by weight solution is 43.73 mN/m.

EXAMPLE 4

Esterification of Inulin with Caprylic Anhydride in Pyridine

In a temperature-controlled reactor with stirrer, 21 g (0.13 moles) of inulin, dissolved in 150 mL of pyridine, are mixed with 3.5 g (0.013 moles) of caprylic anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 75% by weight. The degree of substitution is 0.04 and the surface tension of a 1% by weight solution is 37.33 mN/m.

EXAMPLE 5

Esterification of Inulin with Capric Anhydride in Pyridine

In a temperature-controlled reactor with stirrer, 21 g (0.13 moles) of inulin, dissolved in 150 mL of pyridine, are mixed with 4.2 g (0.013 moles) of capric anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 85% by weight. The degree of substitution is 0.04 and the surface tension of a 1% by weight solution is 34.23 mN/m.

EXAMPLE 6

Esterification of Inulin with Lauric Anhydride in Pyridine

In a temperature-controlled reactor with stirrer, 21 g (0.13 moles) of inulin, dissolved in 150 mL of pyridine, are mixed with 4.9 g (0.013 moles) of lauric anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 80% by weight. The degree of substitution is 0.04 and the surface tension of a 1% by weight solution is 38.17 mN/m.

EXAMPLE 7

Esterification of Inulin with Myristic Anhydride in Pyridine

In a temperature-controlled reactor with stirrer, 21 g (0.13 moles) of inulin, dissolved in 150 mL of pyridine, are mixed with 5.67 g (0.013 moles) of myristic anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 80% by weight. The degree of substitution is 0.04 and the surface tension of a 1% by weight solution is 34.29 mN/m.

EXAMPLE 8

Esterification of Inulin with Palmitic Anhydride in Pyridine

In a temperature-controlled reactor with stirrer, 21 g (0.13 moles) of inulin, dissolved in 150 mL of pyridine, are mixed with 6.4 g (0.013 moles) of palmitic anhydride. After 24 hours at 25° C., the product is precipitated from the reaction mixture with 100 mL of ethyl acetate, filtered off with suction and taken up in 100 mL of water. The suspension obtained is centrifuged and the clear supernatant solution is lyophilized. The product is obtained in a yield of 80% by weight. The degree of substitution is 0.04 and the surface tension of a 1% by weight solution is 30.15 mN/m.

EXAMPLE 9

Esterification of Inulin with Capryl Chloride in Pyridine

In a temperature-controlled reactor with stirrer, 21 g (0.13 moles) of inulin, dissolved in 150 mL of pyridine, are mixed with 83.0 mL (0.4 moles) of capryl chloride. After 24 hours at 40° C., the reaction mixture is hydrolyzed with 100 mL of water and the product is extracted with ethyl acetate (3×100 mL). After the acetate phase is washed with 1M sodium hydroxide solution (3×30 mL) and the ethyl acetate is distilled off under vacuum, the product is obtained as a brown oil, which is decolorized with activated charcoal (yield: 65% by weight, DS 2.5).

EXAMPLE 10

Esterification of Inulin with Stearyl Chloride in Pyridine with 4-(Dimethylamino)-pyridine as Catalyst In a temperature-controlled reactor with stirrer, 15 g (0.09 moles) of inulin, dissolved in 250 mL of pyridine, are mixed with 1.3 g (0.01 moles) of 4-dimethylamino-pyridine and 60 mL (0.18 moles) of stearyl chloride. After 24 hours at 60° C., the reaction mixture is hydrolyzed with 100 mL of water and the product is extracted with ethyl acetate (4×100 mL). After the acetate phase is washed with 1M sodium hydroxide solution (3×30 mL) and with 20 mL of 50% by weight of acetic acid and the ethyl acetate is distilled off under vacuum, the product is obtained as a colorless solid in a yield of 62% by weight and with a DS 1.8.

EXAMPLE 11

Esterification of Inulin with Stearic Anhydride in Pyridine with 4-(Dimethylamino)-pyridine as Catalyst In a temperature-controlled reactor with stirrer, 10 g (0.06 moles) of inulin, dissolved in 100 mL of pyridine, are mixed with 0.6 g (0.005 moles) of 4-dimethylamino-pyridine and 98 g (0.18 moles) of stearic anhydride. After 24 hours at 60° C., the product is hydrolyzed with 100 mL of water and filtered and the filtrate is extracted with ethyl acetate (4×100 mL). After the acetate phase is washed with 20 mL of 50% by weight of acetic acid and the ethyl acetate is distilled off under vacuum, the product is obtained as a colorless solid in a yield of 45% by weight and with a DS of 2.3

EXAMPLE 12

Esterification of Inulin with Isobutyric Anhydride in the Absence of a Solvent and in the Presence of Sodium Acetate In a temperature-controlled reactor with stirrer, a mixture of 15 g (0.09 moles) of inulin and 0.75 g (0.009 moles) of sodium acetate, suspended in 66.5 mL (0.4 moles) of isobutyric anhydride, is heated for 4 hours at 140° C. The excess anhydride is removed under vacuum (15 hPa). The residue is taken up in 100 mL of ethyl acetate, washed with water (3×30 mL), 1M sodium hydroxide solution (3×30 mL) and once again with water (3×30 mL). After removal of the solvent, the product is obtained as a slightly colored oil in a yield of 75% by weight and with a DS of 3.

EXAMPLE 13

Esterification of Inulin with Acetic Anhydride/ Isobutyric Anhydride in the Absence of a Solvent and in the Presence of Sodium Acetate In a temperature-controlled reactor with stirrer, 10 g (0.06 moles) of inulin are suspended in a solution of 10 mL (0.09 moles) of acetic anhydride and 15 mL (0.09 moles) of isobutyric anhydride, mixed with 0.5 g (0.006 moles) of sodium acetate and heated for 4 hours at 140° C. The excess anhydride is removed under vacuum (15 hPa). The residue is taken up in 100 mL of ethyl acetate, washed with water (3×30 mL), 1M sodium hydroxide solution (3×30 mL) and once again with water (3×30 mL). After removal of the solvent, the product is obtained as a slightly colored oil in a yield of 60% by weight and with a DS of 1.5.

EXAMPLE 14

Esterification of Inulin in Water with Propionic Anhydride in the Presence of an Ion Exchange Resin In a temperature controlled reactor with stirrer, 15 g (0.09 moles) of inulin, dissolved in 250 mL of water, are mixed with 12.3 mL (0.09 moles) of propionic anhydride and heated in the presence of 300 g of Merck ion exchange resin III (OH⁻ form) for 24 hours at 40° C. The ion exchange resin is filtered off, the solution is evaporated under vacuum, the residue is suspended in 100 mL of water and the mixture is filtered. From the filtrate, the product is obtained as a colorless solid by freeze drying in a yield of 50% by weight and with a DS of 0.5.

EXAMPLE 15

Esterification of Inulin with Acetic Anhydride in the Absence of a Solvent and the Presence of an Ion Exchange Resin In a temperature controlled reactor with stirrer, 10 g (0.06 moles) of inulin are suspended in 13.5 mL (0.12 moles) of acetic anhydride and heated in the presence of 0.3 g of Amberlite IR 120 (acidic form) for 30 minutes at 100° C. The ion exchange resin is filtered off, the solution is concentrated under vacuum, the residue is suspended in 100 mL of water. From the filtrate of the suspension, the product is obtained as a colorless solid by freeze drying in a yield of 30% by weight and with a DS of 0.8.

EXAMPLE 16

Esterification of Inulin with Capric Chloride in Pyridine

In a temperature controlled reactor with stirrer, 21 g (0.13 moles) of inulin, dissolved in 140 mL of pyridine, are mixed with 13.5 mL (0.065 moles) of capric chloride. After 24 hours at 40° C., the reaction mixture is hydrolyzed with 100 mL of water and extracted with ethyl acetate (4×100 mL). After the ethyl acetate phase is washed with 1M sodium hydroxide solution (3×30 mL) and the ethyl acetate distilled off under vacuum, the product is obtained in a yield of 60% and with a DS of 0.4. The surface tension of a 0.03% by weight solution is 40 mN/m.

EXAMPLE 17

Esterification of Inulin with Stearyl Chloride in Pyridine with 4-(Dimethylamino)-pyridine as Catalyst In a temperature controlled reactor with stirrer, 15 g (0.09 moles) of inulin, dissolved in 150 mL of pyridine, are mixed with 0.7 g (0.005 moles) of 4-(dimethylamino)-pyridine and with 30 mL (0.09 moles) of stearyl chloride. After 24 hours at 60° C., the reaction mixture is hydrolyzed with 100 mL of water and extracted with ethyl acetate (4×100 mL). After the ethyl acetate phase is washed with 1M sodium hydroxide solution (3×30 mL) and the ethyl acetate is distilled off under vacuum, the product is obtained in a yield of 65% with a DS of 0.8. The surface tension of a 0.03% by weight solution is 28 mN/m.

EXAMPLE 18

Esterification of Inulin with Stearic Anhydride in Pyridine with 4-(Dimethylamino)-pyridine as Catalyst In a temperature controlled reactor with stirrer, 21 g (0.13 moles) of inulin, dissolved in 150 mL of pyridine, are mixed with 1.3 g (0.01 moles) of 4-(dimethylamino)-pyridine and with 35 g (0.065 moles) of stearic anhydride dissolved in 150 mL of pyridine. After 24 hours at 60° C., the reaction mixture is hydrolyzed with 200 mL of water and extracted with ethyl acetate (5×100 mL). After the ethyl acetate phase is washed with 1M sodium hydroxide solution (3×30 mL) and the ethyl acetate is distilled off under vacuum, the product is obtained in a yield of 55% with a DS of 0.4. The surface tension of a 0.03% by weight solution is 35 mN/m.

EXAMPLE 19

Solvent-free Acylation of Inulin with Methyl Palmitate

A mixture of 10 kg (60 moles) of inulin, 11.6 kg (43 moles) of methyl palmitate, 1.62 kg (4 moles) of potassium stearate and 0.30 kg (2 moles) of potassium carbonate is extruded by a twin-screw extruder into a reactor and heated for 60 minutes at 100 mbar to 150° C. The crude product obtained is suspended in 200 L of water and filtered and the filtrate is extracted with diethyl ether (4×50 L) and freeze dried. The lyophilisate is extracted in a Soxhlet apparatus for 16 hours with boiling butanol (460 L). The reaction product can be obtained in a yield of 50% by weight from the concentrated extract phase as a slightly colored solid. DS=0.05, surface tension=30.0 mN/m (1% solution).

EXAMPLE 20

Determination of the Surface Tension

The inventive products have a high surface activity already at low degrees of substitution. The surface tension of 1% by weight aqueous inulin ester solutions was measured at 25° C. by the Wilhelmy method. The sample names, listed in the following Table, are supplemented by the degree of substitution, which is given in parentheses.

TABLE 1

| Determination of the Surface Tension | |
|---|---|
| Sample | Surface Tension (mN/m) |
| Inulin acetate (0.03) | 66.43 |
| Inulin acetate (0.7) | 51.14 |
| Inulin butyrate (0.06) | 54.95 |
| Inulin caproate (0.04) | 43.73 |
| Inulin caprylate (0.04) | 37.33 |
| Inulin caprate (0.04) | 34.23 |
| Inulin laurate (0.04) | 38.17 |
| Inulin myristate (0.05) | 34.29 |
| Inulin palmitate (0.05) | 30.15 |

EXAMPLE 21

Solubilization of Sudan Red B in Water with Inulin Esters

Inulin ester solutions of different concentrations (0.06 g, 0.12 g, and 0.24 g each in 20 mL of water) were in each case mixed with 0.01 g of Sudan Red B. The dye was dispersed ultrasonically and the suspension obtained was subsequently centrifuged for 60 minutes at 7000 rpm. The extinction of the clear supernatant solution was measured photometrically at a wavelength of 516 nm in a 1 cm cuvette. A solution of Sudan Red B in water (0.01 g in 20 mL) served as blank.

The results using inulin stearate (with a DS of 0.04) are given by way of example in Table 2. It can be seen that inulin stearate solubilizes the dye. These solubilization properties illustrate the use of inulin esters according to the invention in laundry detergents, detergents and dyeing agents.

TABLE 2

Solubilization

| Inulin Stearate Concentration (% by weight; DS 0.04) | Extinction |
| --- | --- |
| 0 | 0.113 |
| 0.3 | 0.263 |
| 0.6 | 0.400 |
| 1.2 | 0.407 |

EXAMPLE 22

Wetting Properties of Inulin Esters

The wetting of solid surfaces by aqueous solutions of inulin esters were investigated by way of example on glass with a 1% by weight aqueous solution of inulin esters. The measurement was made by the Wilhelmy method, the contact angle, given as the advancing angle, being the variable measured (see Table 3). In comparison to pure water, the inventive inulin esters improve the wetting of glass.

TABLE 3

Wetting of Glass

| Substance | Advancing Angle (°) |
| --- | --- |
| Water | 45 |
| 1% by weight of inulin caproate solution (DS 0.04) | 38 |

EXAMPLE 23

Coating Properties of Inulin Esters

If solids are immersed for prolonged periods in an aqueous solution of inulin esters, the wetting of the solids by water is changed. This is illustrated by the following results. Teflon was used as test object and a 1% by weight of inulin palmitate solution (DS 0.04) was used as inulin ester solution. The immersion period was 30 minutes. The advancing angle was decreased from 88° to 73°.

EXAMPLE 24

Viscosity of Aqueous Inulin Solutions

The viscosity of water is increased by the addition of inulin esters. This is confirmed by measuring the viscosity of aqueous inulin solutions with the Ubbelohde viscosimeter (see Table 4). The temperature was 25° C.

TABLE 4

Viscosity Measurements

| Substance | Concentration ($10^{-1}$ g/mL) | Viscosity (mm$^2$/s) |
| --- | --- | --- |
| Water | — | 0.942 |
| Inulin | 1 | 1.46 |
| Inulin caproate (DS 0.05) | 1 | 1.72 |
| Inulin caproate (DS 0.1) | 1 | 1.79 |
| Inulin stearate (DS 0.04) | 1 | 3.01 |

EXAMPLE 25

Plasticizing Properties of Inulin Esters

If sheets of cellulose acetate are produced in the presence of inulin esters with a high degree of substitution (DS>1) and with short-chain alkyl substituents, the hardness of the sheets is decreased and the flexibility increased. However, the transparency of thesheets is not affected. The results of some investigations are given by way of example in Table 5. The hardness of the sheets was determined by several persons using the finger test and the flexibility was determined using the bending test.

TABLE 5

Plasticizing Test with Cellulose Acetate (1.2 g) and 0.8 g of Plasticizer (LS Inulin: Inulin DP 5–6, DS of the Cellulose Acetate: 2)

| Sheet | Color, Optical Property | Transparency: IR (%) | Hardness | Flexibility |
| --- | --- | --- | --- | --- |
| Cellulose acetate | colorless, clear | 35 | very high | very slight |
| Cellulose acetate + inulin acetate isobutyrate DS 1.4, acetate DS = 0.4 | colorless, clear | 25 | low | high |
| Cellulose acetate + inulin acetate isobutyrate, DS 2, acetate DS 1.7 | colorless, clear | 23 | low | high |
| Cellulose acetate + LS inulin acetate isobutyrate DS 1.4 | colorless, clear | 22 | low | high |
| Cellulose acetate + inulin acetate propionate, DS 1.5 | colorless, clear | 20 | low | high |
| Cellulose acetate + inulin isobutyrate propionate DS 1.4 | colorless, clear | 20 | low | high |
| Cellulose acetate + inulin caproate DS 3 | colorless, clear | 18 | low | high |

EXAMPLE 26

Formulation of a Detergent Formulation for Washing Dishes by Hand

To produce detergent solution according to the invention useful for washing dishes by hand, 30 g of inulin laurate (DS: 0.04) (30% by weight) are mixed with 6 mL of ethanol (6% by weight), 1 g of sodium chloride (1% by weight), 0.5 g of preservative (0.5% by weight) and 0.5 g of perfume oil (0.5% by weight) and made up to 100 g with 62 mL of water (62% by weight).

EXAMPLE 27

Preparation of a Cleansing Cream

To prepare cleansing cream, according to the invention, 8 g (8% by weight) of inulin laurate (DS: 0.04) are mixed with 4 g of cetanol (4% by weight), 3 g of stearic acid (3% by weight), 15 g of paraffin oil (15% by weight), 0.2 g of preservative (0.2% by weight) and 0.3 g of perfume oil (0.3% by weight) and made up to 100 g with 69.5 g of water (69.5% by weight).

EXAMPLE 28

Preparation of a Hair Rinse

To prepare hair rinse, according to the invention, 6 g (6% by weight) of inulin stearate (DS 0.04) are mixed with 6 g of lauryl trimethylammonium chloride (6% by weight), 4 g of stearyl alcohol (4% by weight), 4 g of glycerin (4% by weight), 1 g of citric acid (1% by weight) and 0.5 of perfume oil (0.5% by weight) and made up to 100 g with 78.5 g of water (78.5% by weight).

EXAMPLE 29

Preparation of a Body Lotion

To prepare body lotion, according to the invention, 8 g (8% by weight) of inulin palmitate (DS 0.04) are mixed with 2 g of cetanol (2% by weight), 2 g isopropyl myristate (2% by weight), 4 g of polysiloxane (4% by weight), 4 g of glycerol palmitate (4% by weight), 4 g of 1,2-dihydroxypropane (4% by weight), 3 g of carbomer (3% by weight) and 0.5 g of perfume oil (0.5% by weight) and made up to 100 g with 72.5 g of water (72.5% by weight).

Many variations of the present invention will suggest themselves to those skilled in the art in light of the above-detailed description. Such obvious variations are within the full intended scope of the appended claims.

We claim:

1. An inulin ester comprising at least six monosaccharide units linked together wherein at least one of the inulin hydroxyl groups is esterified with a saturated carboxylic acid and wherein the degree of substitution (DS) is from 0.03 to 0.5.

2. An inulin ester as defined in claim 1 having an average chain length of between about 6 and about 50 monosaccharide units.

3. An inulin ester as defined in claim 1 wherein the carboxylic acid has 2 to 22 carbon atoms.

4. An inulin ester as defined in claim 3 wherein the carboxylic acid has between 2 and 7 carbon atoms.

5. An inulin ester as defined in claim 1 wherein the carboxylic acid is selected from the group consisting of acetic acid, propionic acid, isobutyric acid, butyric acid, valeric acid, caproic acid, heptanoic acid, caprylic acid, capric acid, lauric acid, myristic acid, palmitic acid, stearic acid, arachidic acid or behenic acid, or mixtures thereof.

6. An inulin ester as defined in claim 1 wherein at least two hydroxyl groups are esterified with different carboxylic acids.

7. An inulin ester as defined in claim 1 wherein at least two hydroxyl groups are esterified with identical carboxylic acids.

8. An aqueous solution comprising an inulin ester as defined in claim 1.

9. A powder comprising an inulin ester as defined in claim 1.

10. A cosmetic product comprising an inulin ester as defined in claim 1, wherein said product is selected from the group consisting of a cleansing cream, hair rinse and body lotion.

11. A rinsing agent comprising an insulin ester as defined in claim 1.

12. A method of synthesizing an inulin ester as defined in claim 1 comprising (i) providing inulin having at least 6 fructose units linked to one another; and (ii) reacting the inulin with chlorides or anhydrides of carboxylic acids having 2 to 22 carbon atoms, or mixtures thereof, in the presence of pyridine as the only solvent.

13. A method for synthesizing an inulin ester as defined in claim 1, comprising (i) providing inulin having, at least 6 fructose units linked to one another, and (ii) reacting the inulin with anhydrides of carboxylic acids having 2 to 22 carbon atoms, or mixtures thereof, in the presence of water as the only solvent.

14. A method for synthesizing an inulin ester as defined in claim 1, comprising (i) providing an inulin having at least 6 fructose units linked to one another, and (ii) reacting the inulin with anhydrides of carboxylic acids having 2 to 22 carbon atoms, or mixtures thereof, in the absence of a solvent.

15. A method for synthesizing an inulin ester as defined in claim 1, comprising (i) providing an inulin having at least 6 fructose units linked to one another, and (ii) reacting the inulin with carboxylic esters having 2 to 22 carbon atoms, or mixtures thereof, in the absence of a solvent and in the presence of a catalyst.

16. A method as defined in claim 15, wherein the reacting step is carried out in an extruder or in a kneader.

17. A method as defined in claim 15, wherein the catalyst is a basic or acidic catalyst.

18. A method as defined in claim 17, wherein said catalysts are selected from the group consisting of: 4-(dimethylamino)-pyridine, sodium acetate, potassium carbonate, ion exchangers in the acidic or basic form, and pyridine.

19. A method as defined in claim 12, wherein a catalyst is used in the reacting step.

20. A method as defined in claim 13, wherein a catalyst is used in the reacting step.

21. A method as defined in claim 14, wherein a catalyst is used in the reacting step.

22. The use of inulin esters as defined in claim 1, or mixtures thereof, as surface active substances; as additives in laundry detergent, dishwashing detergent and other detergent; as plasticizers or as auxiliary materials in the paper, textile and paint industries.

* * * * *